(12) United States Patent
Bühler et al.

(10) Patent No.: US 6,794,186 B2
(45) Date of Patent: Sep. 21, 2004

(54) PCAR AND ITS USES

(75) Inventors: Thomas Bühler, Riehen (CH); Reto Andr as Gadient, Newark, DE (US); Reinhard Korn, Freiburg (DE); Rao Movva, Binningen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/899,634

(22) Filed: Jul. 5, 2001

(65) Prior Publication Data

US 2002/0059654 A1 May 16, 2002

(30) Foreign Application Priority Data

Jul. 7, 2000 (GB) .............................................. 0016791

(51) Int. Cl.$^7$ ........................ C12N 15/85; C12N 15/63; C07H 21/04; A01K 67/00
(52) U.S. Cl. ................... 435/325; 435/320.1; 536/23.5; 536/23.1; 536/23.2; 536/24.1; 800/18; 800/3; 800/21
(58) Field of Search .............................. 435/325, 320.1; 536/23.5, 23.1, 23.2, 24.1; 800/18, 3, 21

(56) References Cited

U.S. PATENT DOCUMENTS

| | | | |
|---|---|---|---|
| 4,736,866 A | 4/1988 | Leder et al. | 800/1 |
| 4,870,009 A | 9/1989 | Evans et al. | 435/70 |
| 4,873,191 A | 10/1989 | Wagner et al. | 435/317.1 |

FOREIGN PATENT DOCUMENTS

WO    WO 98/33819 A1 *  8/1998

OTHER PUBLICATIONS

Richards FM. Protein stability: still an unsolved problem. Cell Mol Life Sci. Oct 1997;53(10):790–802.*
Fechner et al. Expression of coxsackie adenovirus receptor and alphav–integrin does not correlate with adenovector targeting in vivo indicating anatomical vector barriers. Gene Ther. 1999 Sep;6(9):1520–35.*
Bergelson JM, et al., "Isolation of a Common Receptor for Coxsackie B Viruses and Adenoviruses 2 and 5", Science, vol. 275, pp. 1320–1323 (1997).
Wickham TJ, et al., "Integrins $\alpha_v\beta_3$ and $\alpha_v\beta_5$ Promote Adenovirus Internalization but Not Virus Attachment", Cell, vol. 73, pp. 309–319 (1993).
Marsden KM, et al., "Transgenic Expression of Embryonic MAP2 in Adult Mouse Brain: Implications for Neuronal Polarization", The Journal of Neuroscience, vol. 16, No. 10, pp. 3265–3273 (1996).
Hogan B, et al., "Manipulating the Mouse Embryo", Production of Transgenic Mice, pp. 219–221 (1986).

* cited by examiner

Primary Examiner—David Guzo
Assistant Examiner—Daniel M. Sullivan
(74) Attorney, Agent, or Firm—Susan Hess

(57) ABSTRACT

The invention provides improvements in the field of animal models for testing effects of genes introduced into animal cells or tissue by adenoviral gene transfer. More particularly the invention provides a plasmid construct that expresses a porcine adenovirus receptor (pCAR) and transgenic animals that show expression of pCAR.

6 Claims, No Drawings

SEQUENCE LISTING

<160> NUMBER OF SEQ ID NOS: 4

<210> SEQ ID NO 1
<211> LENGTH: 4286
<212> TYPE: DNA
<213> ORGANISM: porcine
<220> FEATURE:
<221> NAME/KEY: CDS
<222> LOCATION: (3229)..(4014)

<400> SEQUENCE: 1

```
cggtgcgggc ctcttcgcta ttacgccagc tggcgaaagg gggatgtgct gcaaggcgat        60
taagttgggt aacgccaggg ttttcccagt cacgacgttg taaaacgacg gccagtgcca       120
agttgggatc tttgcattgg cccacggctc tcaggatggg gatgctcccc ttcagcaccc       180
ggttcccctt ggaaactgat ggtcctggct ctgtggcatg gcagtggcac tgtgaggagc       240
ccctaccagc agcacacagt gggtttggca ctgccacgct ccggatgccg cgctctgatc       300 caacccata atcaagggaa cccgaattgc cccatcattg cccccaccac ccccatcctg       360
ccgggccctc acacccacg ctgccttgtg gtgacattcc ccagcccaaa cccacggctt       420
catggctacc gcggggcatt tcccattgcc gccccattat cagctctgca cacctcccgc       480
tgtacccatg cctcgtggct gcccttcttt gacgtataat cttctaatta atacccggcc       540
ttgtcaaagt ggagcacaaa cgttaattaa ttccccagca ggcaggtaat taacagtgtg       600 actcccttt tgctgcgagt ggggctgata cagagagatg tggcactatg gagcccacgg       660
ggtcctggca ctgggtgccc acggaggtcc ccatgtgctg cagtgtcacc gcctccgagg       720
tgacagtatt gtccctgcgg tgtccctgca gctcagctct gtccacaggg ccacctccag       780
tttggagggg acacaatgca gccccgatgc aacccatcct cgcagcatcc cagggacaaa       840 gacccactg caagaccgca cacagggctg ggtcccgctc ccctaatatc tacagtgctt       900
ttgcatggcc ccttaatcaa tgcagttaat cagcatgcgc tcatgcaccg ctctggagct       960
gcaaagcccc tcgcagcgct gctcaccaac accgcgcacc gccccggccc agcctgcagc      1020
acgcgctgca aacaggaaag aaacaaaata ttgcccaaat gtaggcaaag gcattcggct      1080
gccttgacct ccgccgggcc gggccctgcc tgactcagct ccttactcag cgctcgcttc      1140
```

-continued

```
ctccctccgg ctgccaccgc cgcagcgcac accctgacaa agagtggccc ttaacgggct   1200
ctgaggtgca cccagcagtg cactcagcag tccaagggcc ggcctggagg tttgcaccgc   1260
tacgtgctga cattagcatt gaacttggcc ctgggtagtg ctgcaggccg ggcggggtgg   1320
gtgtagagag tgcagcgcgc gttgcacccg gtgccccttc ccctcccttg catcccagca   1380
ggctgcaccc cagcaccagg cccgtgcatg catgctcctg gtgttattgc agcctggtgc   1440
atgcatgcgt cttagtggtg cagcgctgtg catgcatcct ccttggtgtg tagcagctta   1500
gtgcatgcat acccctcggt gttattgctg ctctgtgcac gcacgctcat tgtatcactt   1560
catcccagtg catgcactca cactggagcg attgctgctc ggtgcacgca cactcattgt   1620
atcacgtcag ctcagtggct gcacgcacac cggtgttatt gctgctcggt gcgtgcatgc   1680
acatcagtgt cgctgcagct cagtgcatgc acgctcattg cccatcgcta tccctgcctc   1740
tcctgctggc gctccccggg aggtgacttc aaggggaccg caggaccacc tcggggggtgg   1800 ggggagggct gcacacgcgg accccgctcc ccctccccaa caaagcactg tggaatcaaa   1860
aaggggggag gggggatgga ggggcgcgtc acacccccgc cccacaccct cacctcgagg   1920
tgagccccac gttctgcttc actctcccca tctccccccc ctccccaccc ccaattttgt   1980
atttatttat ttttttaatta tttttgtgcag cgatggggc ggggggggg gggcgcgcg    2040 ccaggcgggg cggggcgggg cgaggggcgg ggcggggcga ggcggagagg tgcggcggca   2100
gccaatcaga gcggcgcgct ccgaaagttt cctttatgg cgaggcggcg gcggcggcgg   2160
ccctataaaa agcgaagcgc gcggcgggcg ggagtcgctg cgttgccttc gccccgtgcc   2220
ccgctccgcg ccgcctcgcg ccgcccgccc cggctctgac tgaccgcgtt actcccacag   2280
gtgagcgggc gggacggccc ttctcctccg ggctgtaatt agcgcttggt ttaatgacgg   2340
ctcgtttctt ttctgtggct gcgtgaaagc cttaaagggc tccgggaggg cccttttgtgc   2400 gggggggagc ggctcggggg gtgcgtgcgt gtgtgtgtgc gtggggagcg ccgcgtgcgg   2460
cccgcgctgc ccggcggctg tgagcgctgc gggcgcggcg cggggctttg tgcgctccgc   2520
gtgtgcgcga ggggagcgcg gccggggggcg gtgccccgcg gtgcgggggg gctgcgaggg   2580
gaacaaaggc tgcgtgcggg gtgtgtgcgt gggggggtga gcaggggggtg tgggcgcggc   2640 ggtcgggctg taaccccccc ctgcaccccc ctccccgagt tgctgagcac ggcccggctt   2700
cgggtgcggg gctccgtgcg gggcgtggcg cggggctcgc cgtgccgggc gggggtggc   2760 ggcaggtggg ggtgccgggc ggggcggggc cgcctcgggc cggggagggc tcggggggagg   2820 ggcgcggcgg ccccggagcg ccggcggctg tcgaggcgcg gcgagccgca gccattgcct   2880
tttatggtaa tcgtgcgaga gggcgcaggg acttcctttg tcccaaatct ggcggagccg   2940
aaatctggga ggcgccgccg caccccctct agcgggcgcg ggcgaagcgg tgcggcgccg   3000
gcaggaagga aatgggcggg gagggccttc gtgcgtcgcc gcgccgccgt ccccttctcc   3060
atctccagcc tcgggctgc cgcaggggga cggctgcctt cggggggggac ggggcagggc   3120 ggggttcggc ttctgcgtg tgaccggcgg ggtttatatc ttcccttctc tgttcctccg   3180
cagcccccaa gcttaaggtg cacggcccac gtggggacta gtgccacc atg gcg ctc    3237
                                                    Met Ala Leu
                                                     1 ctg ctg tgc ttc gtg ctc ctg tgc gga gtc gcg gat ctc acc aga agt    3285
Leu Leu Cys Phe Val Leu Leu Cys Gly Val Ala Asp Leu Thr Arg Ser
 5                  10                  15 ttg agt atc act act cct gaa cag atg att gaa aag gcc aaa ggg gaa    3333
Leu Ser Ile Thr Thr Pro Glu Gln Met Ile Glu Lys Ala Lys Gly Glu
```

-continued

| | 20 | | | 25 | | | | 30 | | | | 35 | | | |
|---|---|---|---|---|---|---|---|---|---|---|---|---|---|---|---| act gcc tat ttg cca tgc aga ttt acc ctg ggt cca gaa gac cag ggg      3381
Thr Ala Tyr Leu Pro Cys Arg Phe Thr Leu Gly Pro Glu Asp Gln Gly
                40                  45                  50 ccg ctg gac atc gag tgg ctg ctg tca cca gct gat aat cag aag gtg      3429
Pro Leu Asp Ile Glu Trp Leu Leu Ser Pro Ala Asp Asn Gln Lys Val
            55                  60                  65 gat caa gtg att att tta tat tct gga gac aaa att tat gac gac tac      3477
Asp Gln Val Ile Ile Leu Tyr Ser Gly Asp Lys Ile Tyr Asp Asp Tyr
        70                  75                  80 tac caa gat ctg aaa gga cga gta cat ttt aca agt aat gat ctc aaa      3525
Tyr Gln Asp Leu Lys Gly Arg Val His Phe Thr Ser Asn Asp Leu Lys
    85                  90                  95 tca ggt gat gca tca ata aat gta aca aat cta cag ttg tca gat att      3573
Ser Gly Asp Ala Ser Ile Asn Val Thr Asn Leu Gln Leu Ser Asp Ile
100                 105                 110                 115 ggc aca tat cag tgc aaa gtg aaa aag gct cct ggt gtt gga aat aag      3621
Gly Thr Tyr Gln Cys Lys Val Lys Lys Ala Pro Gly Val Gly Asn Lys
                120                 125                 130 aag att cag ctg aca gtt ctt ctt aag cct tca ggt aca aga tgt tat      3669
Lys Ile Gln Leu Thr Val Leu Leu Lys Pro Ser Gly Thr Arg Cys Tyr
            135                 140                 145 gtt gat gga tca gaa gaa att gga aat gac ttt aaa cta aaa tgt gaa      3717
Val Asp Gly Ser Glu Glu Ile Gly Asn Asp Phe Lys Leu Lys Cys Glu
        150                 155                 160 cca aaa gaa ggt tca ctc cca tta cta tat gaa tgg cag aaa ttg tcc      3765
Pro Lys Glu Gly Ser Leu Pro Leu Leu Tyr Glu Trp Gln Lys Leu Ser
    165                 170                 175 aat tca cag aag ctg ccc acc ttg tgg tta gca gaa atg act tca cct      3813
Asn Ser Gln Lys Leu Pro Thr Leu Trp Leu Ala Glu Met Thr Ser Pro
180                 185                 190                 195 gtt ata tct gta aaa aat gcc tct act gaa tac tct ggg aca tac agc      3861
Val Ile Ser Val Lys Asn Ala Ser Thr Glu Tyr Ser Gly Thr Tyr Ser
                200                 205                 210 tgt acc gtg aaa aac aga gtg ggc tct gat cag tgc ctg ctt cgc ctg      3909
Cys Thr Val Lys Asn Arg Val Gly Ser Asp Gln Cys Leu Leu Arg Leu
            215                 220                 225 gat gtg gtt cct cct tca aat aga gct gga aca att gca gga gct gtt      3957
Asp Val Val Pro Pro Ser Asn Arg Ala Gly Thr Ile Ala Gly Ala Val
        230                 235                 240 ata gga gtt ttg ctt gct cta gtg ctc att ggt ctt atc atc ttt tgc      4005
Ile Gly Val Leu Leu Ala Leu Val Leu Ile Gly Leu Ile Ile Phe Cys
    245                 250                 255 tgt cgt taa tctagataag taatgatcat aatcagccat atcacatctg               4054
Cys Arg
260 tagaggtttt acttgcttta aaaaacctcc cacacctccc cctgaacctg aaacataaaa     4114 tgaatgcaat tgttgttgtt aacttgttta ttgcagctta taatggttac aaataaagca     4174 atagcatcac aaatttcaca aataaagcat ttttttcact gcattctagt tgtggtttgt     4234 ccaaactcat caatgtatct tatcatgtct ggatccccgg gtaccgagct cg             4286

<210> SEQ ID NO 2
<211> LENGTH: 261
<212> TYPE: PRT
<213> ORGANISM: porcine

<400> SEQUENCE: 2

Met Ala Leu Leu Leu Cys Phe Val Leu Leu Cys Gly Val Ala Asp Leu

```
                1               5                   10                  15
        Thr Arg Ser Leu Ser Ile Thr Thr Pro Glu Gln Met Ile Glu Lys Ala
                        20                  25                  30

Lys Gly Glu Thr Ala Tyr Leu Pro Cys Arg Phe Thr Leu Gly Pro Glu
                        35                  40                  45

Asp Gln Gly Pro Leu Asp Ile Glu Trp Leu Leu Ser Pro Ala Asp Asn
                        50                  55                  60

Gln Lys Val Asp Gln Val Ile Ile Leu Tyr Ser Gly Asp Lys Ile Tyr
         65                  70                  75                  80

Asp Asp Tyr Tyr Gln Asp Leu Lys Gly Arg Val His Phe Thr Ser Asn
                        85                  90                  95

Asp Leu Lys Ser Gly Asp Ala Ser Ile Asn Val Thr Asn Leu Gln Leu
                       100                 105                 110

Ser Asp Ile Gly Thr Tyr Gln Cys Lys Val Lys Lys Ala Pro Gly Val
                       115                 120                 125

Gly Asn Lys Lys Ile Gln Leu Thr Val Leu Leu Lys Pro Ser Gly Thr
                       130                 135                 140

Arg Cys Tyr Val Asp Gly Ser Glu Ile Gly Asn Asp Phe Lys Leu
        145                 150                 155                 160

Lys Cys Glu Pro Lys Glu Gly Ser Leu Pro Leu Leu Tyr Glu Trp Gln
                       165                 170                 175

Lys Leu Ser Asn Ser Gln Lys Leu Pro Thr Leu Trp Leu Ala Glu Met
                       180                 185                 190

Thr Ser Pro Val Ile Ser Val Lys Asn Ala Ser Thr Glu Tyr Ser Gly
                       195                 200                 205

Thr Tyr Ser Cys Thr Val Lys Asn Arg Val Gly Ser Asp Gln Cys Leu
                       210                 215                 220

Leu Arg Leu Asp Val Val Pro Pro Ser Asn Arg Ala Gly Thr Ile Ala
        225                 230                 235                 240

Gly Ala Val Ile Gly Val Leu Leu Ala Leu Val Leu Ile Gly Leu Ile
                       245                 250                 255

Ile Phe Cys Cys Arg
                       260

<210> SEQ ID NO 3
<211> LENGTH: 1098
<212> TYPE: DNA
<213> ORGANISM: porcine
<220> FEATURE:
<221> NAME/KEY: CDS
<222> LOCATION: (1)..(1098)

<400> SEQUENCE: 3 atg gcg ctc ctg ctg tgc ttc gtg ctc ctg tgc gga gtc gcg gat ctc      48
Met Ala Leu Leu Leu Cys Phe Val Leu Leu Cys Gly Val Ala Asp Leu
1               5                   10                  15 acc aga agt ttg agt atc act act cct gaa cag atg att gaa aag gcc      96
Thr Arg Ser Leu Ser Ile Thr Thr Pro Glu Gln Met Ile Glu Lys Ala
                20                  25                  30 aaa ggg gaa act gcc tat ttg cca tgc aga ttt acc ctg ggt cca gaa     144
Lys Gly Glu Thr Ala Tyr Leu Pro Cys Arg Phe Thr Leu Gly Pro Glu
            35                  40                  45 gac cag ggg ccg ctg gac atc gag tgg ctg ctg tca cca gct gat aat     192
Asp Gln Gly Pro Leu Asp Ile Glu Trp Leu Leu Ser Pro Ala Asp Asn
        50                  55                  60 cag aag gtg gat caa gtg att att tta tat tct gga gac aaa att tat     240
Gln Lys Val Asp Gln Val Ile Ile Leu Tyr Ser Gly Asp Lys Ile Tyr
```

-continued

```
                65                  70                  75                  80
gac gac tac tac caa gat ctg aaa gga cga gta cat ttt aca agt aat         288
Asp Asp Tyr Tyr Gln Asp Leu Lys Gly Arg Val His Phe Thr Ser Asn
                    85                  90                  95 gat ctc aaa tca ggt gat gca tca ata aat gta aca aat cta cag ttg         336
Asp Leu Lys Ser Gly Asp Ala Ser Ile Asn Val Thr Asn Leu Gln Leu
                100                 105                 110 tca gat att ggc aca tat cag tgc aaa gtg aaa aag gct cct ggt gtt         384
Ser Asp Ile Gly Thr Tyr Gln Cys Lys Val Lys Lys Ala Pro Gly Val
            115                 120                 125 gga aat aag aag att cag ctg aca gtt ctt ctt aag cct tca ggt aca         432
Gly Asn Lys Lys Ile Gln Leu Thr Val Leu Leu Lys Pro Ser Gly Thr
        130                 135                 140 aga tgt tat gtt gat gga tca gaa gaa att gga aat gac ttt aaa cta         480
Arg Cys Tyr Val Asp Gly Ser Glu Glu Ile Gly Asn Asp Phe Lys Leu
145                 150                 155                 160 aaa tgt gaa cca aaa gaa ggt tca ctc cca tta cta tat gaa tgg cag         528
Lys Cys Glu Pro Lys Glu Gly Ser Leu Pro Leu Leu Tyr Glu Trp Gln
                    165                 170                 175 aaa ttg tcc aat tca cag aag ctg ccc acc ttg tgg tta gca gaa atg         576
Lys Leu Ser Asn Ser Gln Lys Leu Pro Thr Leu Trp Leu Ala Glu Met
                180                 185                 190 act tca cct gtt ata tct gta aaa aat gcc tct act gaa tac tct ggg         624
Thr Ser Pro Val Ile Ser Val Lys Asn Ala Ser Thr Glu Tyr Ser Gly
            195                 200                 205 aca tac agc tgt acc gtg aaa aac aga gtg ggc tct gat cag tgc ctg         672
Thr Tyr Ser Cys Thr Val Lys Asn Arg Val Gly Ser Asp Gln Cys Leu
        210                 215                 220 ctt cgc ctg gat gtg gtt cct cct tca aat aga gct gga aca att gca         720
Leu Arg Leu Asp Val Val Pro Pro Ser Asn Arg Ala Gly Thr Ile Ala
225                 230                 235                 240 gga gct gtt ata gga gtt ttg ctt gct cta gtg ctc att ggt ctt att         768
Gly Ala Val Ile Gly Val Leu Leu Ala Leu Val Leu Ile Gly Leu Ile
                    245                 250                 255 gtg ttt tgc tgt cat aaa aag cgc aga gaa gaa aaa tac gaa aaa gaa         816
Val Phe Cys Cys His Lys Lys Arg Arg Glu Glu Lys Tyr Glu Lys Glu
                260                 265                 270 gtg cat cat gat atc agg gaa gac gtg cct cct ccg aag agc aga acg         864
Val His His Asp Ile Arg Glu Asp Val Pro Pro Pro Lys Ser Arg Thr
            275                 280                 285 tcc act gcc aga agc tac ctc ggc agc aac cac tcg tcc ctg gga tcc         912
Ser Thr Ala Arg Ser Tyr Leu Gly Ser Asn His Ser Ser Leu Gly Ser
        290                 295                 300 atg tct cct tcc aac atg gaa ggc tat tcc aag act cag tat aac cag         960
Met Ser Pro Ser Asn Met Glu Gly Tyr Ser Lys Thr Gln Tyr Asn Gln
305                 310                 315                 320 gta cca agc gaa gac ttt gaa cgc gct cct cag agt cca act ctc ccg        1008
Val Pro Ser Glu Asp Phe Glu Arg Ala Pro Gln Ser Pro Thr Leu Pro
                    325                 330                 335 ctc gct aag gta gct gcc cct aat ctc agc cgg atg gga gcg gtg cct        1056
Leu Ala Lys Val Ala Ala Pro Asn Leu Ser Arg Met Gly Ala Val Pro
                340                 345                 350 gtg atg att cca gcc cag agc aag gac ggg tcc ata gta taa              1098
Val Met Ile Pro Ala Gln Ser Lys Asp Gly Ser Ile Val
            355                 360                 365
```

<210> SEQ ID NO 4
<211> LENGTH: 365
<212> TYPE: PRT
<213> ORGANISM: porcine

```
<400> SEQUENCE: 4

Met Ala Leu Leu Leu Cys Phe Val Leu Leu Cys Gly Val Ala Asp Leu
1               5                   10                  15

Thr Arg Ser Leu Ser Ile Thr Thr Pro Glu Gln Met Ile Glu Lys Ala
            20                  25                  30

Lys Gly Glu Thr Ala Tyr Leu Pro Cys Arg Phe Thr Leu Gly Pro Glu
            35                  40                  45

Asp Gln Gly Pro Leu Asp Ile Glu Trp Leu Leu Ser Pro Ala Asp Asn
        50                  55                  60

Gln Lys Val Asp Gln Val Ile Ile Leu Tyr Ser Gly Asp Lys Ile Tyr
65                  70                  75                  80

Asp Asp Tyr Tyr Gln Asp Leu Lys Gly Arg Val His Phe Thr Ser Asn
                85                  90                  95

Asp Leu Lys Ser Gly Asp Ala Ser Ile Asn Val Thr Asn Leu Gln Leu
            100                 105                 110

Ser Asp Ile Gly Thr Tyr Gln Cys Lys Val Lys Lys Ala Pro Gly Val
            115                 120                 125

Gly Asn Lys Lys Ile Gln Leu Thr Val Leu Leu Lys Pro Ser Gly Thr
        130                 135                 140

Arg Cys Tyr Val Asp Gly Ser Glu Ile Gly Asn Asp Phe Lys Leu
145                 150                 155                 160

Lys Cys Glu Pro Lys Glu Gly Ser Leu Pro Leu Leu Tyr Glu Trp Gln
            165                 170                 175

Lys Leu Ser Asn Ser Gln Lys Leu Pro Thr Leu Trp Leu Ala Glu Met
            180                 185                 190

Thr Ser Pro Val Ile Ser Val Lys Asn Ala Ser Thr Glu Tyr Ser Gly
            195                 200                 205

Thr Tyr Ser Cys Thr Val Lys Asn Arg Val Gly Ser Asp Gln Cys Leu
        210                 215                 220

Leu Arg Leu Asp Val Val Pro Pro Ser Asn Arg Ala Gly Thr Ile Ala
225                 230                 235                 240

Gly Ala Val Ile Gly Val Leu Leu Ala Leu Val Leu Ile Gly Leu Ile
            245                 250                 255

Val Phe Cys Cys His Lys Lys Arg Arg Glu Glu Lys Tyr Glu Lys Glu
            260                 265                 270

Val His His Asp Ile Arg Glu Asp Val Pro Pro Lys Ser Arg Thr
            275                 280                 285

Ser Thr Ala Arg Ser Tyr Leu Gly Ser Asn His Ser Ser Leu Gly Ser
        290                 295                 300

Met Ser Pro Ser Asn Met Glu Gly Tyr Ser Lys Thr Gln Tyr Asn Gln
305                 310                 315                 320

Val Pro Ser Glu Asp Phe Glu Arg Ala Pro Gln Ser Pro Thr Leu Pro
            325                 330                 335

Leu Ala Lys Val Ala Ala Pro Asn Leu Ser Arg Met Gly Ala Val Pro
            340                 345                 350

Val Met Ile Pro Ala Gln Ser Lys Asp Gly Ser Ile Val
            355                 360                 365
```

PCAR AND ITS USES

The invention provides improvements in the field of animal models for testing effects of genes introduced into animal cells or tissue by adenoviral gene transfer.

Adenoviruses infect cells using two cell surface receptors, the "Coxsackie B and adenovirus 2 and 5 receptor" (hereinafter referred to as CAR; Bergelson J. M., et al, Science 275, 1320–23, 1997) and the integrin receptors ($\alpha v \beta 3$ or $\alpha v \beta 5$; Wickham, T. J. et al, Cell 73, 309–19, 1993) the contents thereof being incorporated herein by reference. Adenoviral based vectors are widely used in gene therapy, as they represent one of the most efficient ways to deliver genes to target cells. They are of particular interest for in vivo gene therapy proof-of concept experiments in rodent models. However, rodent tissues are not well transducible with adenoviral vectors.

In its broad aspect the invention is concerned with genetic modification of target cells which are normally refractory to adenoviral transduction. More particularly the invention provides a plasmid construct that expresses a porcine adenovirus receptor (PCAR) and transgenic animals that show expression of pCAR.

Organ transplants of liver, kidney, lung and heart are now regularly performed as treatment for endstage organ disease. Despite the use of modern immunosuppressive drugs acute and chronic graft (tissue or organ) rejection still remain major factors in graft loss. There is, therefore, a continued need for means to inhibit acute and chronic graft rejection and increase graft acceptance, e.g. through induction of peripheral tolerance without causing serious toxic side effects typically associated with conventional immunosuppressant therapy. When considering cell transplantation, e.g. bone marrow derived cells, islet cells, neuronal cells etc. one is faced with similar problems of rejection. Making organs or cells less immunogenic through genetic modification is seen as an alternative or add on to conventional immunosuppression.

Rodent animal models are of crucial importance for testing the immunomodulatory effects of new gene products. However in the case of using adenovirus as gene delivery vehicle rodent models have so far proven to be of limited value, as many rodent organs or cell types are refractory to adenoviral transduction. This may be due to the fact that either the adenoviral receptor CAR is not expressed or only weakly expressed on the cell surface of the cells of interest.

Accordingly, the invention provides a plasmid or vector construct that comprises a DNA molecule which expresses porcine CAR (SEQ ID NO:4 hereinafter referred to as pCAR) or a biologically active fragment or derivative thereof, for example a C-terminally truncated porcine CAR (SEQ ID NO:2hereinafter referred to as $\Delta$pCAR), that retains full functionality as adenoviral receptor.

pCAR comprises an intracellular domain, a transmembrane domain and a an extracellular domain that binds to the adenoviral fibre proteins, i.e. a total sequence of 365 amino-acids. It will be understood that any nucleic acid sequence encoding a porcine CAR homologue is a candidate for utilization in the present invention. For example, it may include a pCAR sequence with a modified, mutated or truncated region thereof, that retains the activity of mediating adenoviral transduction. It will be further understood by the skilled person that any nucleic acid sequence which encodes a biologically active form of pCAR, including but not limited to a genomic or cDNA sequence or functionally equivalent variant or mutant thereof or a fragment thereof which encodes a biologically active protein fragment or derivative which mediates adenoviral transduction, may be utilized in the present invention. For example, $\Delta$pCAR may comprise the leader sequence of 19 amino-acids, the extracellular domain of 216 amino-acids, the transmembrane domain of 24 amino-acids and a truncated cytoplasmic domain, e.g. limited to 3 amino-acids. Two potential sites for N-glycosylation are located at Asn 106 and Asn 201. Aminoacids present in the sequence which are not essential to the activity may be changed by mutation, e.g. amino-acid 258 may be changed from Val to Ile; amino-acid 262 may be changed from His to Arg.

Preferred nucleic acid sequence for use in the invention is e.g. as disclosed in SEQ ID NO: 1 from nucleotide 3229 to nucleotide 4014. The corresponding amino acid sequence encoded by such DNA sequence is indicated in SEQ ID NO:2.

Any known expression vector or plasmid that is capable of expression upon transfection of a specified eukaryotic target cell may be utilized to pratice the invention. "Plasmid" and "vector" can be used interchangeably in the present specification as the plasmid is the most commonly used form of vector. An expression vector is a vector capable of directing the expression of genes to which they are operatively linked. An operable linkage as used herein refers to the position, orientation and linkage between a structural gene and expression control element(s) such that the structural gene can be expressed in any host cell. The term "expression control element" includes promoters, enhancers, ribosome binding sites etc. Any eukaryotic promoter and/or enhancer sequences available to the skilled person which are known to control expression of the nucleic acid of interest may be used in plasmid vector constructs, including but not limited to a cytomegalovirus (CMV) promoter, a Rous Sarcoma (RVS) promoter, a Murine Leukemia (MLV) promoter, a herpes simplex virus (HVS) promoter, such as HSV-tk, a $\beta$-actin promoter, e.g. chicken $\beta$-actin, as well as any additional tissue specific or signal specific regulatory sequence that induces expression in the target cell or tissue of interest. A preferred expression vector or plasmid according to the invention is e.g. an eukaryotic expression vectors, e.g. a p$\beta$-actin-p16PL vector such as p(chicken)$\beta$-actin-p16PL.

In one such embodiment, a DNA sequence encoding pCAR is subcloned into the DNA plasmid expression vector, e.g. p$\beta$-actin-p16PL, resulting in p$\beta$-actin-pCAR-p16PL. p16PL is a standard mammalian expression vector, containing a gene that encodes a selectable marker, e.g. an antibiotic resistance gene, and a $\beta$-actin promoter active in mammalian cells (K. M. Marsden et al, J. Neurosc., May 15, 1996, 16(10): 3265–3273). Such a construct, which may be constructed by one of ordinary skill with components available from numerous sources, will drive expression of a pCAR DNA fragment ligated downstream of the $\beta$-actin promoter subsequent to transfection of the target cell. More specifically, pCAR is cloned from pig liver RNA using a PCR based approach. The PCR fragment is inserted into the expression vector pSport (Life Technologies). This plasmid serves as template to create the truncated version of $\Delta$pCAR. Preferably p$\beta$-actin is p$\beta$-(chicken) actin.

The invention further provides host cells into which a recombinant expression vector of the invention has been introduced. A host cell can be any prokaryotic or eukaryotic cell, e.g. bacterial such as *E. Coli*, yeast or mammalian cells, e.g. CHO or COS cells.

The host cells of the invention may preferably be used to produce nonhuman transgenic animals, preferably a mammal, more preferably a rodent such as a rat or mouse, or a pig.

For example, a host cell of the invention is a fertilized oocyte or an embryonic stem cell into which a pCAR-coding sequence has been introduced. A transgenic animal of the invention, more preferably a mammal, most preferably a rodent or a pig, may be created by introducing a pCAR expression construct into the male pronuclei of a fertilized oocyte, e.g. by microinjection, or into embryonic stem cells, e.g. by electroporation. Methods for generating transgenic rodents have become conventional in the art and are described e.g. in U.S. Pat. Nos. 4,736,866, 4,870,009, 4,873, 191, or in Manipulating the Mouse Embryo, B. Hogan, (Cold Spring Harbor Laboratory Press, Cold Spring Harbor, N.Y., 1986). For example the expression construct may be introduced into an embryonic stem cell line and cells in which the introduced pCAR gene has integrated are selected. The selected cells are then used to produce chimaeras with known standard procedures. A chimaeric embryo can then be implanted into a suitable pseudopregnant female foster animal and the embryo brought to term. The pCAR expression plasmid may also be inserted into somatic/body cells of the donor animal to provide a somatic recombinant animal, from whom the DNA construct is not capable of being passed on to offspring. For example, a somatic cell from the transgenic animal can be isolated and induced to exit the growth cycle and enter $G_o$ phase. The quiescent cell can then be fused, e.g. through the use of electrical pulses, to an enucluated oocyte from an animal of the same species from which the quiescent cell is isolated. The reconstructed oocyte is then cultured such that it develops to morula or blastocyst and then transferred to pseudopregnant female foster animal. The offspring of this female foster animal will be a clone of the animal from which the somatic cell is isolated. Or for example, an improved method of cloning pigs using donor nuclei from non-quiescent differentiated cells in which the desired DNA, e.g. porcine CAR or fragments or variants thereof, is inserted in said differentiated pig cell or pig cell nucleus. This improved method is described in U.S. Pat. No. 6,235, 969 B1 and is hereby incorporated by reference.

The present invention also provides a method for improving adenoviral gene transfer in a rodent using a transgenic rodent which expresses or overexpresses pCAR. Such rodents may be used as models in gene therapy to test adenoviral transduction, e.g. prevention or treatment of acute or chronic graft rejection, autoimmune disorders, e.g rheumatoid arthritis, cardiovascular disorders, e.g. restenosis, nervous system disorders, e.g. parkinson disease, etc. A preferred embodiment of the invention is the use of such rodents expressing or overexpressing pCAR in transplantation experiments, for example, of organs, tissues or cells, e.g. lung, heart, kidney, liver, pancreas, small bowel, spleen, pancreatic islets, neuronal or stem cells, etc. For example, organs, tissues or cells of such transgenic rodents, e.g. mice, are removed, in vitro transduced with the adenoviral gene delivery vector to be tested and then transplanted into rodents, e.g. mice, e.g. such animals which do not express pCAR.

The functional expression of pCAR, e.g. ΔpCAR may also be used to generate transgenic pigs that overexpress this adenoviral receptor. Porcine organs, tissues or cells transgenically modified to express high levels of pCAR may be used as recipients for adenoviral gene therapy vectors. Such transgenic modified organs, tissues or cells can be transfected with adenoviral gene therapy vectors carrying thrapeutically beneficial genes either ex vivo or in vivo and can be subsequently transplanted in a recipient. Beneficial genes are those that are expected to confer graft protection following transplantation of these gene delivered organs in xenotransplantation therapy. The present invention comprises a method to generate such transgenic pigs expressing high levels of pCAR or a functionally equivalent variant or mutant thereof or a fragment thereof, e.g. as disclosed above, and gene therapy methods for preventing or inhibiting graft rejection in a recipient using organs, tissues or cells of such transgenic pigs.

Definitions

To facilitate understanding of the invention, a number of terms are defined below.

"Fragment" of a polypeptide sequence refers to a polypeptide sequence that is shorter than the reference sequence but that retains essentially the same biological function or activity as the reference polypeptide. "Fragment" of a polynucleotide sequence refers to a polynuclotide sequence that is shorter than the reference sequence of SEQ ID NO:2 and 4.

"Transduction" Transfer of genetic material or characteristics from one bacterial cell to another by the incorporation of bacterial DNA into a bacteriophage.

"Variant" refers to a polynucleotide or polypeptide that differs from a reference polynucleotide or polypeptide, but retains the essential properties thereof. A typical variant of a polynucleotide differs in nucleotide sequence from the reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from the reference polypeptide. Generally, alterations are limited so that the sequences of the reference polypeptide and the variant are closely similar overall and, in many regions, identical. A variant and reference polypeptide may differ in amino acid sequence by one or more substitutions, insertions, deletions in any combination. A substituted or inserted amino acid residue may or may not be one encoded by the genetic code. Typical conservative substitutions include Gly, Ala; Val, lie, Leu; Asp, Glu; Asn, Gln-I Ser, Thr; Lys, Arg; and Phe and Tyr. A variant of a polynucleotide or polypeptide may be naturally occurring such as an allele, or it may be a variant that is not known to occur naturally. Non-naturally occurring variants of polynucleotides and polypeptides may be made by mutagenesis techniques or by direct synthesis. Also included as variants are polypeptides having one or more post-translational modifications, for instance glycosylation, phosphorylation, methylation, ADP ribosylation and the like. Embodiments include methylation of the N-terminal amino acid, phosphorylations of serines and threonines and modification of C-terminal glycines.

The following Examples are illustrative only and not limiting of the invention. The β-actin promotor used in the Examples is the β-(chicken)actin promotor.

EXAMPLE 1

Construction of the Expression Vector

The full length cDNA for porcine CAR is cloned from pig liver using degenerated primers (forward: 5'-accatggcgckcctrctgt-3' (SEQ ID NO:5) and reverse: 5'-catatggaggctytatacya-3' (SEQ ID NO: 6) in which k=g or t; r=a or g and y=c or t)). The PCR fragment is bluntend inserted into the vector pSport (Life Technologies). Porcine CAR (SEQ ID NO:4) has an overall amino acid homology of 91% to human as well as mouse CAR. This clone is used as template to generate the ΔpCAR gene as disclosed in SEQ ID NO: 1 from nucleotide 3229 to nucleotide 4014, using PCR. The primers used to generate this construct contain two amino acid changes at the C-terminal end of the construct. The sense primer SpeI-CAR (5'-ggactagtgccaccatggcgctcctgctgtgcttc-3', SEQ ID NO:7) is located at position 1-21 of pCAR and contains a SpeI site, a Kozak sequence and the start codon. The antisense primer CAR-XbaI (5'-gctctagattaacgacagcaaaagatgataagacc-3', SEQ ID NO:8) is located at position 760–786 of porcine CAR containing a stop codon and a XbaI site. The PCR amplification used the following conditions: 1× native Pfu buffer, 2.5 mM $MgCl_2$, 0.2 mM dNTPs, 2.5 U native Pfu polymerase (Stratagene) and 20 pmol SpeI-CAR and CAR-XbaI (each). Porcine CAR cDNA (5 ng) is used as template and hot start PCR is performed using the following profile: 1× (5 min 95° C.) 20× (30 sec 95° C., 1 min 55° C., 1 min 30 sec 72° C.) 1× (3 min 72° C.). A PCR product of a predicted size of 788 bps is obtained and separated on a 1% low melting agarose gel (SeaPlaque GTG; FMC). The band is excised and the PCR product isolated from the gel piece using the QIAquick gel extraction kit from Qiagen according to the manufacturers protocol. The isolated PCR product is then digest with XbaI (LifeTechnologies) and repurified as described above. The digested purified PCR product is ligated into MscI-XbaI digested pβactin-16PL vector.

IN VαF' chemically ultracompetent bacteria from invitrogen are transformed and 48 colonies picked, rescreened by PCR using SpeI-CAR and CAR-XbaI as primers. From 48 colonies analyzed 20 contain the insert-12 are selected for DNA sequencing. The sequencing primer actinsense (5'accggcggggtttatatcttc-3', SEQ ID NO:9) is the 5-primer located just upstream of the MCS of the pβactin-16PL vector. Actinanti (5'-cctctacagatgtgatatggc-3', SEQ ID NO: 10) is the 3-primer located just downstream of the MCS of pβactin-16PL vector. The nucleotide sequence of the β-actin promoter, the ΔpCAR gene and the SV40 polyadenylation signal is shown in SEQ ID NO:1.

EXAMPLE 2

In Vitro Expression of ΔpCAR in Mammalian Cells (Western Blot)

A human lung carcinoma cell (A30), rat embryonic fibroblasts (Rat2, ATCC:CRL-1764) and chinese hamster ovary cells (CHO) are used for transient transfections. Culture conditions are as follows:

| Cell Line | Medium | Serum | Supplement | Antibiotics |
| --- | --- | --- | --- | --- |
| A30 | RPMI | 10% FBS | 1% NEAA | 1% PS |
| Rat2 | DMEM | 10% FBS | | 1% PS |
| CHO | αMEM | 10% FBS | | 1% PS |

In addition, all media contain 2 mM Glutamax II. Cultures are maintained at 37° C. in a water saturated air atmosphere containing 5% $CO_2$.

Cells are transfected with either the control plasmid (pβactin-16PL vector) or pβactin-ΔpCAR-16PL. In brief, an 80% confluent (approx. 1×10⁸ cells) 15 cm dish is transfected with 15 μg plasmid DNA using SuperFect from Qiagen according to the manufacturers protocol. After 24 h, cells are harvested, washed and cell pellet resuspended in 0.5 ml Lämmli's buffer. Western blotting supplies are obtained from BioRad unless otherwise stated. Samples are sonicated for 10 sec, heat-denatured for 5 min at 95° C. and cellular debris removed by centrifugation (10 min 13 krpm Eppendorf). Samples are stored at −20° C. until further use. A quantity of 30 μl/lane is loaded on to a 12% denaturing polyacrylamide gel (SDS-PAGE) and run at 100V for 90 min in 1×Tris/Glycine/SDS buffer. Gel is then electrotransfered onto a 0.45 μm Protan BA85 (Schleicher&Schuell) nitrocellulose membrane in 1×Tris/Glycine buffer (Novex) containing 20% methanol. The membrane is blocked for 1 h in phosphate-buffered saline (PBS) containing 5% non-fat dry milk and 1%Tween 20 (Sigma), followed by 1 h incubation with an affinity-purified polyclonal chicken-anti human CAR antibody at 1:500 in blocking solution. In between antibody incubation steps the membrane is washed by two short rinses in PBS/1%Tween 20 followed by 2×15 min in the same washing buffer. The membrane is incubated for 1 h with a biotinylated rabbit-anti chicken IgY (Vector Laboratories) diluted at 1:1000 in blocking solution, followed by 30 min incubation with streptavidin-horseradish peroxidase (Vector Laboratories) at 1:1000 in blocking solution. Membrane is incubated for 5 min in enhanced chemiluminescence (ECL) substrate (Amersham), solution is carefully drained and membrane put in a Photogene Development folder (Life Technologies). ECL signals are detected by exposing Hyperfilm ECL (Amersham) to the membrane and films are developed on a X-Ray film developer (Agfa).

All 3 different cell lines which are transfected with ΔpCAR-16PL show an additional strong protein band which has the predicted molecular size. As a positive control 100 ng of recombinant human soluble CAR (hCAR) purified from E.coli source is used.

The polyclonal chicken-anti human CAR antibody used above are prepared as follows: A soluble version of human CAR is generated by PCR using the CAR1 (5'-accggccatggcatatggatttcgccagaa-3', SEQ ID NO:11) and the CAR2 (5'-accggctcgagagctttatttgaaggagggac-3', SEQ ID NO:12) primers. As template full length human CAR cloned from HeLa cells is used. The soluble human CAR PCR fragment is digested with Nde 1 and Xho1 and inserted into the prokaryotic expression vector pET-17H, which contains a C-terminal histidine tag. The construct is transformed into bacteria and cells are induced to produce the soluble human CAR protein. The protein is purified by commonly used methods and is injected into an adult female chick. The eggs of the hen are collected and antibodies isolated from the egg yolk.

EXAMPLE 3

Functionality of ΔpCAR in Mammalian Cells (Adenoviral Gene Transfer)

The functionality is tested by transient transfection of CHO cells with the construct to be tested or the control plasmid, followed by transduction with an adenovirus which contains a reporter gene.

CHO cells are seeded into 24 well plate at a density of 12,000 cells/well. Cells are transiently transfected with 0.5 μg plasmid DNA of either pβactin-16PL or pβactin-ΔpCAR-16PL and incubated for 24 h. Cells are then transduced with an adenoviral vector carrying β-galactosidase as a reporter gene (moi 0–100) for 2 h. Virus solution is removed and cells incubated for an additional 4 days. Reporter gene expression is monitored using staining for nuclear β-galactosidase. Only ΔpCAR transfected cells are transduced with the reporter gene.

EXAMPLE 4

Generation of Transgenic Mice (a) Generation of ΔpCAR BALB/c ES Cell Lines $5 \times 10^8$ BALB/c ES cells ("Efficient targeting of the IL-4 gene in a BALB/c embryonic stem cell line", Noben-Trauth et al, Transgenic-Res. 1996 Nov; 5(6): 487–91) are electroporated with 30 μg of the linearized construct. Transfected cells are selected with G418 (200 μg/ml). G418-resistant clones are screened for integration events by PCR. The ES cells are lysed 1 h/37° C. with 20 μl Lysis buffer (PCR buffer 1×; SDS 1.7 μM; Proteinase K 50 μg/ml) heat inactivated 85° C./15 Min. and cleared by centrifugation. 1,3 μl lysed solution is used in for a 50 μl PCR. Positive clones are further verified by Southern analysis.

(b) Generation of ΔpCAR Transgenic Mice

BALB/c-ES cell clones carrying one ΔpCAR allele are injected into C57BL/6 host blastocysts and transferred into pseudopregnant foster mothers according to standard protocols. Chimaeras are mated with BALB/c females and albino offspring (indicative for germ line transmission) are analyzed by PCR for target integration and Southern analysis. Heterozygous animals are generated by back-crossing of F1 animals to Balb/c wild type animals and Southern analysis of the F2 animals. The homozygous lines are established by mating heterozygous F1 animals.

EXAMPLE 5

Transplantation

Hearts of transgenic mice obtained according to Example 4 are removed, in vitro transduced by infusion with an adenovirus carrying β-galactosidase and then heterotopically transplanted into female mice (which do not express PCAR). Age matched Balb/c male mice are used as controls. 4 days after transplantation hearts are removed, perfusion stained for nuclear β-galactosidase, paraffin embedded and sectioned. Sections are counterstained with hematoxylin and evaluated by light microscopy. Positive expression for β-galactosidase is seen in the transgenic mice compared to the control animals.

What is claimed is:

1. An isolated DNA sequence which encodes a C-terminally truncated porcine coxsackie and adenovirus receptor (pCAR) having the amino acid sequence as set forth in SEQ ID NO:2.

2. A plasmid or vector construct that comprises a DNA which expresses a C-terminally truncated porcine CAR according to claim 1.

3. An isolated host cell into which a vector according to claim 2 has been introduced.

4. The isolated DNA sequence of claim 1, wherein the isolated DNA sequence has the sequence of SEQ ID NO:1 from nucleotide 3229 to nucleotide 4014.

5. The isolated DNA sequence of claim 1, wherein the asparagine at amino acid positions 106 and 201 is glycosylated.

6. An isolated DNA sequence which encodes a C-terminally truncated porcine coxsackie and adenovirus receptor (pCAR) having the amino acid sequence as set forth in SEQ ID NO: 2, with the exception that the amino acid at position 258 is isoleucine instead of valine and the amino acid at position 262 is arginine instead of histidine.

* * * * *